(12) United States Patent
Ito et al.

(10) Patent No.: US 11,702,684 B2
(45) Date of Patent: Jul. 18, 2023

(54) METHOD FOR MEASURING PROTEIN AND NUCLEIC ACID WITH ULTRAHIGH SENSITIVITY

(71) Applicant: BioPhenoMA Inc, Tokyo (JP)

(72) Inventors: Etsuro Ito, Hokkaido (JP); Toshiaki Miura, Sapporo (JP); Teruki Yoshimura, Sapporo (JP); Satoshi Watabe, Ito (JP)

(73) Assignee: BioPhenoMA Inc., Tokyo (JP)

( * ) Notice: Subject to any disclaimer, the term of this patent is extended or adjusted under 35 U.S.C. 154(b) by 1177 days.

(21) Appl. No.: 16/089,488

(22) PCT Filed: Mar. 7, 2017

(86) PCT No.: PCT/JP2017/008982
§ 371 (c)(1),
(2) Date: Sep. 28, 2018

(87) PCT Pub. No.: WO2017/169565
PCT Pub. Date: Oct. 5, 2017

(65) Prior Publication Data
US 2019/0106727 A1    Apr. 11, 2019

(30) Foreign Application Priority Data

Mar. 30, 2016  (JP) ................. 2016-068686

(51) Int. Cl.

| | | |
|---|---|---|
| *C12Q 1/32* | (2006.01) | |
| *C12Q 1/00* | (2006.01) | |
| *G01N 21/78* | (2006.01) | |
| *G01N 33/569* | (2006.01) | |
| *G01N 33/58* | (2006.01) | |
| *G01N 33/53* | (2006.01) | |
| *G01N 33/535* | (2006.01) | |
| *C12Q 1/68* | (2018.01) | |
| *G01N 21/25* | (2006.01) | |

(52) U.S. Cl.
CPC .............. *C12Q 1/32* (2013.01); *C12Q 1/008* (2013.01); *C12Q 1/68* (2013.01); *G01N 21/78* (2013.01); *G01N 33/53* (2013.01); *G01N 33/535* (2013.01); *G01N 33/5695* (2013.01); *G01N 33/581* (2013.01); *G01N 21/25* (2013.01); *G01N 2333/35* (2013.01); *G01N 2333/90209* (2013.01)

(58) Field of Classification Search
CPC ............ C12Q 1/6816; C12Q 2563/125; C12Q 1/008; C12Q 1/32; C12Q 1/68; G01N 21/78; G01N 2333/35; G01N 33/53; G01N 33/535; G01N 33/5695; G01N 33/573; G01N 33/581
See application file for complete search history.

(56) References Cited

U.S. PATENT DOCUMENTS

| 5,633,143 | A | * | 5/1997 | Ueda ........................ C12Q 1/32 |
|---|---|---|---|---|
| | | | | 436/63 |
| 9,851,309 | B2 | * | 12/2017 | Ito ............................ C12Q 1/34 |
| 11,221,299 | B2 | * | 1/2022 | Ito .......................... C12Q 1/008 |
| 2014/0017675 | A1 | * | 1/2014 | Ito .......................... G01N 21/78 |
| | | | | 552/641 |

FOREIGN PATENT DOCUMENTS

| EP | 0632133 A1 * | 6/1993 |
|---|---|---|
| JP | 11-18798 A | 1/1999 |
| JP | 2001-161399 A | 6/2001 |
| WO | 93/12254 A1 | 6/1993 |

(Continued)

OTHER PUBLICATIONS

A printout retrieved from https://en.wikipedia.org/wiki/List_of_EC_numbers_(EC_1) on Aug. 4, 2022.*
Japanese Office Action, dated Feb. 25, 2020, issued in the corresponding Japanese patent application No. 2016-068686.
Japanese Office Action, dated Aug. 4, 2020, issued in the corresponding Japanese patent application No. 2016-068686.
Extended European Search Report, dated Oct. 17, 2019, issued in the corresponding European patent application No. 17774110.5.
Watabe, S. et al., "Ultrasensitive enzyme-linked immunosorbent assay (ELISA) of proteins by combination with the thio-NAD cycling method" Biophysics (2014) 10:49-54.
Watabe, S., et al., "Ultrasensitive detection of proteins and sugars at single-cell level" Commun. Integr. Biol. (2016) 9 (1):e1124201.
Nakatsuma, A., et al., "Detection of HIV-1 p24 at Attomole Level by Ultrasensitive ELISA with Thio-NAD Cycling" PLoS One (2015) 10(6):e0131319.

(Continued)

*Primary Examiner* — Galina M. Yakovleva
(74) *Attorney, Agent, or Firm* — Robert C. Netter, Jr.; Dann, Dorfman, Herrell & Skillman

(57) ABSTRACT

The present invention pertains to an enzymatic measurement method using an antibody-enzyme complex or a nucleic acid probe measurement method using an enzyme-labeled nucleic acid probe, in both of which the quantification of a product of a reaction by an enzyme in the antibody-enzyme complex or the enzyme-labeled nucleic acid probe is performed by generating thio-NAD(P)H by an enzymatic cycling reaction using NAD(P)H, thio-NAD(P), and a dehydrogenase (DH), and measuring the amount of the generated thio-NAD(P)H or measuring a change in color caused by the generated thio-NAD(P)H. An enzymatic reaction system in which NAD(P) generated from NAD(P)H by the enzymatic cycling reaction is selectively reduced, is caused to coexist with the enzymatic cycling reaction. The present invention also pertains to a kit for enzyme immunoassay, and a kit for nucleic acid probe measurement. In the enzymatic cycling reaction, the detection sensitivity is increased by increasing the amount of thio-NAD(P)H generated per unit time with respect to a predetermined amount of a substrate (reduced), and combining the same with an enzyme immunoassay, etc., enables quantification, etc., of a protein or nucleic acid with high sensitivity.

3 Claims, 5 Drawing Sheets

(56) References Cited

FOREIGN PATENT DOCUMENTS

WO      2008/117816 A1    10/2008
WO      2012/128338 A1     9/2012

OTHER PUBLICATIONS

International Preliminary Reporton Patentability, PCT/JP2017/008982, dated Oct. 2, 2018.
International Search Report and Written Opinion, PCT/JP2017/008982, dated Apr. 18, 2017.
European Office Action, dated Dec. 11, 2020, issued in the corresponding European patent application No. 17774110.5.

* cited by examiner

METHOD FOR MEASURING PROTEIN AND NUCLEIC ACID WITH ULTRAHIGH SENSITIVITY

The present application is § 371 application of PCT/JP2017/08982 filed Mar. 7, 2017 which claims priority to JP Application No. JP2016-068686 filed Mar. 30, 2016, the entire disclosure of each being incorporated by reference herein.

TECHNICAL FIELD

The present invention relates to a method for measuring proteins and nucleic acids with ultrahigh sensitivity. More specifically, the present invention relates to a measurement method and kit for measuring proteins and nucleic acids with ultrahigh sensitivity using enzyme immunoassay and nucleic acid probe assay methods. In particular, the present invention relates to a method and kit whereby amplification of thio-NAD(P)H by thio-NAD cycling is further enhanced in a method that allows a target protein and nucleic acid to be measured with ultrahigh sensitivity by amplifying thio-NAD(P)H by a thio-NAD cycling method in which the substrate is an enzyme reaction product produced by an enzyme labeled antibody or nucleic acid probe.

CROSS-REFERENCE TO RELATED APPLICATIONS

This application claims benefit of priority to Japanese Patent Application No. 2016-068686 filed on Mar. 30, 2016, which is expressly incorporated herein by reference in its entirety.

BACKGROUND ART

In recent years, highly sensitive measurement of proteins and nucleic acids is mainly being performed by methods that do not use radioactive substances. A typical method for measuring proteins is enzyme immunoassay (ELISA), while methods using Polymerase Chain Reaction (PCR) are being used to measure nucleic acids. The sensitivity of immunoassay methods has progressed from early colorimetric methods ($10^{-13}$ mole) to fluorescent methods to light emission methods ($10^{-15}$ mole), and specialized measurement equipment has been developed and improved. However, although measurement procedures have been simplified the degree of sensitivity has reached a limit. In highly sensitive methods of measuring nucleic acids by PCR, meanwhile, quantification of nucleic acids is fundamentally difficult when target-specific signal detection problems, amplification efficiency problems and the conditions under which the PCR product reaches a plateau and the like are considered together.

WO 2008-117816 (PTL 1) and WO 2012-128338 (PTL 2) describe an enzymatic measurement method using an antibody-enzyme complex and a nucleic acid probe measurement method using an enzyme-labeled nucleic acid probe with thio-NAD cycling methods.
PTL 1: WO 2008-117816
PTL 2: WO 2012-128338
PTL1 and PTL2 are expressly incorporated herein by reference in their entirety.

SUMMARY OF INVENTION

Technical Problem

The method described in PTL 1 combines an enzyme immunoassay method with an enzymatic cycling method in which the substrate is the product of a labeling enzyme used in the enzyme immunoassay. With this combination, a protein or nucleic acid can be assayed or detected visually with high sensitivity by colorimetric methods by amplifying thio-NAD(P)H by geometric progression as a signal substance.

The method described in PTL 2 is an improved method that avoids the reactivity between the labeling enzyme and the substrate and the partial inhibition of the enzyme reaction by the substrate for the labeling enzyme in the enzymatic cycling reaction that occur in the method described in PTL 1.

However, there is demand for methods that further increase the detection sensitivity in the methods described in PTL 1 and 2. Possible methods for increasing detection sensitivity within the scope of the methods described in PTL 1 and 2 include optimizing the conditions for the enzyme immunoassay in the first stage, and optimizing the conditions for enzymatic cycling in the second stage for example. The inventors in this case investigated optimizing the conditions in the enzymatic cycling method, and problems with this approach. The basic principles of enzymatic cycling are described here. A substrate (reduced) is produced by the enzyme immunoassay or nucleic acid probe method in the first stage, thio-NAD(P)H having absorbance at 400 nm is generated from this substrate (reduced), NAD(P)H and thio-NAD(P)$^+$, and the generated amount of thio-NAD(P)H is assayed or detected visually.

[C1]

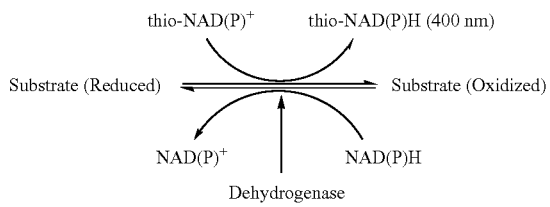

In this enzymatic cycling reaction system, the detection sensitivity is greater the greater the amount of thio-NAD(P)H generated relative to a fixed amount of the substrate (reduced), and the operation time can be reduced if this can be accomplished in a shorter amount of time.

Further researches by the inventors in this case have shown that in this enzymatic cycling reaction system, dehydrogenase tends to be inhibited as the amount of NAD(P)H increases, while if the amount of NAD(P)H is less the NAD(P)H in the reaction system is exhausted at an early stage, the reacted amount from thio-NAD(P)$^+$ to thio-NAD(P)H is small, and detection sensitivity cannot be increased because too little thio-NAD(P)H is produced. It has been found that this problem can be solved by increasing the added amounts of thio-NAD(P)$^+$ and NAD(P)H without changing their relative proportions. If the added amount of thio-NAD(P)$^+$ is increased, however, coloration occurs even before the reaction starts due to light absorption (400 nm) by the thio-NAD(P)$^+$, creating a new problem of coloration with blank samples, so this method is not suited to increasing detection sensitivity.

Under these circumstances, it is an object (problem to be solved) of the present invention to provide a method whereby a protein or nucleic acid can be assayed or detected visually with greater sensitivity than before by increasing the produced amount of thio-NAD(P)H per unit time relative to a fixed amount of the substrate (reduced) to thereby increase detection sensitivity, and then combining this with an enzyme immunoassay method or the like.

Moreover, if the produced amount of thio-NAD(P)H per unit time can be increased, this means that it is possible to reduce the time require to reach the same amount of thio-NAD(P)H production, and thus reduce the operating time.

The inventors performed various experimental studies aimed at solving these problems. As a result, we perfected the present invention after discovering that these problems could be solved by including in the enzymatic cycling reaction system a system that generates (regenerates) NAD(P)H by reducing the $-\text{NAD(P)}^+$ generated in the enzymatic cycling reaction, without affecting the reaction between the thio-NAD(P)$^+$ and thio-NAD(P)H.

Solution to Problem

The present invention is as follows.

[1] An enzymatic measurement method using an antibody-enzyme complex, the method being implemented in which an enzyme reaction product of the antibody-enzyme complex is assayed by generating thio-NADH and/or thio-NADPH by an enzymatic cycling reaction using NADH and/or NADPH, thio-NAD and/or thio-NADP and a dehydrogenase (DH), and then either measuring the generated thio-NADH and/or thio-NADPH, or else measuring a color change caused by the generated thio-NADH and/or thio-NADPH, wherein an enzyme reaction system that selectively reduces the NAD and/or NADP generated from NADH and/or NADPH by the enzymatic cycling reaction is included in the enzymatic cycling reaction system.

[2] The method according to [1], wherein the enzyme reaction system that selectively reduces the NAD and/or NADP uses a substrate that does not become a substrate for the enzyme of the antibody-enzyme complex and a substrate for the enzyme of the enzymatic cycling reaction, and an enzyme that does not react with the substrate for the enzyme of the antibody-enzyme complex and the substrate of the enzyme of the enzymatic cycling reaction.

[3] A nucleic acid probe measurement method using an enzyme-labeled nucleic acid probe, the method being implemented in which an enzyme reaction product of the enzyme-labeled nucleic acid probe is assayed by generating thio-NADH and/or thio-NADPH by an enzymatic cycling reaction using NADH and/or NADPH, thio-NAD and/or thio-NADP and a dehydrogenase (DH), and then either measuring the generated thio-NADH and/or thio-NADPH or else measuring a color change caused by the generated thio-NADH and/or thio-NADPH, wherein an enzyme reaction system that selectively reduces the NAD and/or NADP generated from NADH and/or NADPH by the enzymatic cycling reaction is included in the enzymatic cycling reaction system.

[4] The method according to [3], wherein the enzyme reaction system that selectively reduces the NAD and/or NADP uses a substrate that does not become a substrate for the enzyme of the enzyme-labeled nucleic acid probe and a substrate for the enzyme of the enzymatic cycling reaction, and an enzyme that does not react with the substrate for the enzyme of the enzyme-labeled nucleic acid probe and the substrate of the enzyme of the enzymatic cycling reaction.

[5] The method according to any one of [1] to [4], wherein the enzyme of the enzyme reaction system that selectively reduces the NAD and/or NADP is a dehydrogenase.

[6] The method according to any one of [1] to [5], wherein the enzyme in the enzymatic cycling reaction is a hydroxysteroid dehydrogenase, and the enzyme in the enzyme reaction system that selectively reduces the NAD and/or NADP is a dehydrogenase that is not a hydroxysteroid dehydrogenase.

[7] The method according to any one of [1] to [6], wherein the enzyme in the enzymatic cycling reaction system is a hydroxysteroid dehydrogenase, and the enzyme in the enzyme reaction system that selectively reduces the NAD and/or NADP is an enzyme selected from the enzyme group represented by EC number 1.1.1 having CH—OH as an electron donor, the enzyme group represented by EC number 1.2.1 having an aldehyde or oxo group as an electron donor, the enzyme group represented by EC number 1.3.1 having CH—CH as an electron donor, the enzyme group represented by EC number 1.4.1 having CH—$NH_2$ as an electron donor, and the enzyme group represented by EC number 1.5.1 having CH—NH as an electron donor.

[8] The method according to any one of [1] to [7], wherein the enzyme of the antibody-enzyme complex or the enzyme of the enzyme-labeled nucleic acid probe is at least one of enzyme selected from the group consisting of alkaline phosphatases, glucosidases, galactosidases, fructosidases, mannosidases and peroxidases.

[9] An enzyme immunoassay kit containing reagents (1) to (6) below:

(1) an enzyme labeling an antibody specific to a target protein antigen;

(2) a substrate for the enzyme of (1) above;

(3) a dehydrogenase;

(4) NADH and/or NADPH;

(5) thio-NAD and/or thio-NADP; and (6) an enzyme reaction system that selectively reduces NAD and/or NADP.

[10] A nucleic acid probe measurement kit containing reagents (1) to (6) below:

(1) an enzyme labeling a nucleic acid probe that binds specifically to a target nucleic acid;

(2) a substrate for the enzyme of (1) above;

(3) a dehydrogenase;

(4) NADH and/or NADPH;

(5) thio-NAD and/or thio-NADP; and (6) an enzyme reaction system that selectively reduces NAD and/or NADP.

[11] The kit according to [9] or [10], wherein the enzyme of the enzyme reaction system of (6) above is a dehydrogenase.

[12] The kit according to any one of [9] to [11], wherein in the enzyme reaction system of (6) the substrate does not become a substrate for the enzyme of (1) and a substrate for the dehydrogenase of (3), and the enzyme does not react with the substrate of (2) and with the thio-NAD and/or thio-NADP of (5).

[13] The kit according to any one of [9] to [12], wherein the dehydrogenase of (3) above is a hydroxysteroid dehydrogenase (HSD), and the enzyme of the enzyme reaction system of (6) above is a dehydrogenase that is not a HSD (hydroxysteroid dehydrogenase).

[14] The kit according to any one of [9] to [13], wherein the enzyme in the enzyme reaction system of (6) is an enzyme selected from the enzyme group represented by EC number 1.1.1 having CH—OH as an electron donor, the enzyme group represented by EC number 1.2.1 having an aldehyde or oxo group as an electron donor, the enzyme group represented by EC number 1.3.1 having CH—CH as an electron donor, the enzyme group represented by EC number 1.4.1 having CH—NH$_2$ as an electron donor, and the enzyme group represented by EC number 1.5.1 having CH—NH as an electron donor.

[15] The kit according to any one of [9] and [11] to [14], wherein the enzyme of the antibody-labeling enzyme of (1) is at least one kind of enzyme selected from the group consisting of alkaline phosphatases, glucosidases, galactosidases, fructosidases, mannosidases and peroxidases.

[16] The kit according to any one of [10] to [14], wherein the enzyme of the nucleic acid probe-labeling enzyme of (1) is at least one kind of enzyme selected from the group consisting of alkaline phosphatases, glucosidases, galactosidases, fructosidases, mannosidases and peroxidases.

Advantageous Effects of Invention

Provided are an enzyme immunoassay method and nucleic acid probe measurement method whereby a protein or nucleic acid can be assayed or detected visually with greater sensitivity than in conventional methods.

DESCRIPTION OF EMBODIMENT

Figure 1:
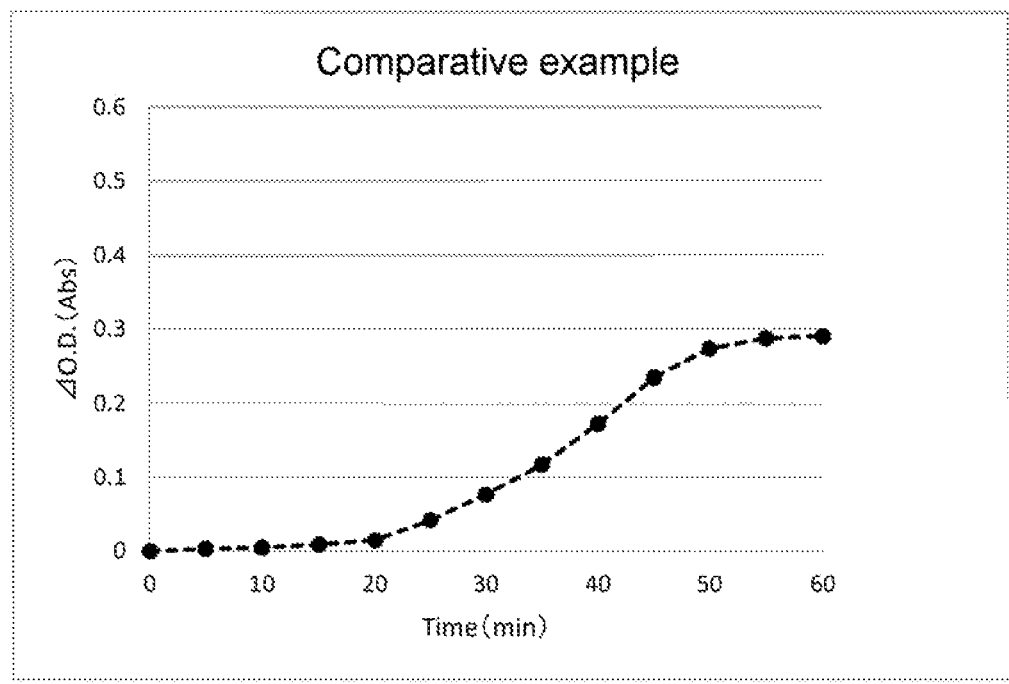
FIG. 1 shows measurement results for a comparative example (conventional method).

In the present Description, NAD(P)$^+$ means the same as NAD and/or NADP, NAD(P)H means the same as NADH and/or NADPH, thio-NAD(P)$^+$ means the same as thio-NAD and/or thio-NADP, and thio-NAD(P)H means the same as thio-NADH and/or thio-NADPH. DH means dehydrogenase.

(Methods of the Invention)

The present invention relates to an enzyme immunoassay method using an antibody-enzyme complex and a nucleic acid probe measurement method using an enzyme-labeled nucleic acid probe (these are generally called the "method of the invention" hereunder). The reaction product of the enzyme of the antibody-enzyme complex in the enzyme immunoassay and the reaction product of the enzyme of the enzyme-labeled nucleic acid probe in the nucleic acid probe measurement method are assayed by first producing thio-NADH and/or thio-NADPH by an enzymatic cycling reaction using NADH and/or NADPH, thio-NAD and/or thio-NADP and a dehydrogenase (DH), and then either measuring the generated thio-NADH and/or thio-NADPH or else measuring a color change caused by the generated thio-NADH and/or thio-NADPH.

The antibody-enzyme complex used in the method of the invention comprises an enzyme labeling an antibody specific to a target protein antigen. The enzyme-labeled nucleic acid probe comprises an enzyme labeling a nucleic acid probe that binds specifically to a target nucleic acid. The enzyme (labeling enzyme) of the antibody-enzyme complex or enzyme-labeled nucleic acid probe can be at least one kind of enzyme selected from the group consisting of the transferase group represented by EC numbers 2., the hydrolase group represented by EC numbers 3.—, the lyase group represented by EC numbers 4.—and the isomerase group represented by EC numbers 5.—for example. Paragraphs 0020 to 0024 of the PTL 1 may be consulted for specific examples of these enzymes.

More specifically, the enzyme (labeling enzyme) of the antibody-enzyme complex or enzyme-labeled nucleic acid probe used in the method of the invention may be an alkaline phosphatase (ALP), galactosidase, glucosidase, fructosidase, mannosidase or peroxidase for example. Paragraphs 0024 to 0027 of the PTL 2 may be consulted for methods of using these enzymes.

Examples of typical combinations of labeling enzymes, substrates and dehydrogenases for enzyme cycling that can be used in the present invention may be found in Paragraphs 0044 to 0051 of the PTL 2, but of course are not limited to these combinations.

The method of the present invention may be implemented in the same way as an ordinary immunoassay or nucleic acid probe method. For example, an antibody or nucleic acid probe that binds specifically to an object of analysis may be immobilized on the surface of a solid carrier, which may be a microplate or plastic tube, magnetic beads or another solid carrier used in ordinary measurement.

The antibody-enzyme complex and nucleic acid probe-enzyme complex may be prepared by ordinary methods.

The antibody of the antibody-enzyme complex may be selected appropriately from antibodies that bind specifically to the object of analysis to be measured by the enzyme immunoassay method of the present invention. For example, the enzyme immunoassay method of the invention is used to analyze proteins, and in this case the antibody of the antibody-enzyme complex is an antibody that binds specifically to a protein to be analyzed. Moreover, in this case a substrate having the antibody that binds specifically to the protein to be analyzed immobilized thereon is used. Furthermore, the antibody constituting the antibody-enzyme complex and the antibody immobilized on the substrate may also be antibody fragments. The object of analysis in the enzyme immunoassay method of the invention need not be a protein, and may be any substance other than a protein that is an object of analysis in ordinary enzyme immunoassay methods.

For the nucleic acid probe-enzyme complex, a probe complementary to a nucleic acid that is an object of analysis may be selected appropriately in the same way.

The reaction product of the enzyme of the antibody-enzyme complex or the enzyme of the enzyme-labeled nucleic acid probe in the method of the present invention is assayed by generating thio-NADH and/or thio-NADPH by an enzymatic cycling reaction using NADH and/or NADPH, thio-NAD and/or thio-NADP and a dehydrogenase (DH), and either measuring the generated thio-NADH and/or thio-NADPH or else measuring a color change caused by the generated thio-NADH and/or thio-NADPH.

A feature of the method of the present invention is that an enzyme reaction system that selectively reduces the NAD and/or NADP produced from NADH and/or NADPH by the enzymatic cycling reaction is included in the enzymatic cycling reaction system. The "selectively" in the enzyme reaction system that selectively reduces NAD and/or NADP means that the co-existing thio-NAD and/or thio-NADP are substantially not reduced.

In the method of the invention, a protein or nucleic acid can be assayed or detected visually with greater sensitivity than in conventional methods because a system that generates (regenerates) NAD(P)H by reducing the NAD(P) produced in the enzymatic cycling reaction without affecting the reaction between the thio-NAD(P)$^+$ and thio-NAD(P)H is included in the enzymatic cycling reaction system.

In this enzyme reaction system, the substrate in the immunoassay method of the invention is preferably one that does not become a substrate for the enzyme of the antibody-enzyme complex and a substrate for the enzyme of the enzyme cycling system, and the enzyme is preferably an enzyme that does not react with the substrate for the enzyme of the antibody-enzyme complex and the substrate of the enzyme of the enzyme cycling system. Moreover, in the nucleic acid probe measurement method the substrate of this enzyme reaction system is preferably one that does not become a substrate for the enzyme of the enzyme-labeled nucleic acid probe and a substrate for the enzyme of the enzyme cycling system, and the enzyme is preferably an enzyme that does not react with either the substrate for the enzyme of the enzyme-labeled nucleic acid probe and the substrate for the enzyme of the enzymatic cycling reaction.

The reaction used to selectively reduce NAD and/or NADP in the present invention is performed with an oxidoreductase having NAD and/or NADP as an electron receptor. Of the oxidoreductases, a dehydrogenase is preferred. This is because the enzyme used in the enzymatic cycling reaction is also a dehydrogenase, and it is desirable that the optimal conditions be equivalent.

The enzyme of the enzyme reaction system that selectively reduces NAD and/or NADP is preferably a dehydrogenase. However, since the enzyme of the enzymatic cycling reaction is also a dehydrogenase, the dehydrogenase that is the enzyme of the enzyme reaction system that selectively reduces NAD and/or NADP and the dehydrogenase that is the enzyme of the enzyme cycling system are selected from dehydrogenases having different substrate specificities. Since the dehydrogenase that is the enzyme of the enzyme cycling system is preferably a hydroxysteroid dehydrogenase, in this case the enzyme of the enzyme reaction system that selectively reduces NAD and/or NADP is selected from those dehydrogenases that are not hydroxysteroid dehydrogenases and that have different substrate specificities from hydroxysteroid dehydrogenases.

The enzyme of the enzymatic cycling reaction system is a dehydrogenase and preferably a hydroxysteroid dehydrogenase, while the enzyme of the enzyme reaction system that selectively reduces NAD and/or NADP is an enzyme having substrate specificities different from those of the dehydrogenases, preferably selected from the enzyme group represented by EC number 1.1.1 having CH—OH as an electron donor, the enzyme group represented by EC number 1.2.1 having an aldehyde or oxo group as an electron donor, the enzyme group represented by EC number 1.3.1 having CH—CH as an electron donor, the enzyme group represented by EC number 1.4.1 having CH—NH$_2$ as an electron donor, and the enzyme group represented by EC number 1.5.1 having CH—NH as an electron donor.

Examples of dehydrogenases belonging to the enzyme group represented by EC number 1.1.1 include malate dehydrogenase, D-3-hydroxybutyrate dehydrogenase, lactate dehydrogenase, alcohol dehydrogenase, glycerol dehydrogenase, iditol-2-dehydrogenase, galactitol dehydrogenase, glycerate dehydrogenase, isocitrate dehydrogenase, gulonate 3-dehydrogenase, ribitol-2-dehydrogenase, gluconate-5-dehydrogenase, 3-isopropyl malate dehydrogenase, glucose dehydrogenase, galactose dehydrogenase and the like.

Examples of dehydrogenases belonging to the enzyme group represented by EC number 1.2.1 include aldehyde dehydrogenase, malonate semialdehyde dehydrogenase, succinate semialdehyde dehydrogenase and the like.

Examples of dehydrogenases belonging to the enzyme group represented by EC number 1.3.1 include dihydrouracil dehydrogenase, acyl CoA dehydrogenase, prephenate dehydrogenase and the like.

Examples of dehydrogenases belonging to the enzyme group represented by EC number 1.4.1 include glutamate dehydrogenase, leucine dehydrogenase, alanine dehydrogenase, phenylalanine dehydrogenase, serine dehydrogenase, valine dehydrogenase, glycine dehydrogenase, lysine dehydrogenase, tryptophan dehydrogenase, aspartate dehydrogenase and the like.

Examples of dehydrogenases belonging to the enzyme group represented by EC number 1.5.1 include methylene tetrahydrofolate dehydrogenase, saccharopin dehydrogenase, D-octopine dehydrogenase and the like.

As discussed above, the enzyme that reduces NAD and/or NADP is selected appropriately after considering the substrate specificity of the dehydrogenase used in the enzymatic cycling reaction and the like. Because substrate specificity may be reduced if the substrate used in the enzymatic cycling reaction is structurally similar to the substrate for the enzyme that reduces NAD and/or NADP, these are selected appropriately so that the respective enzyme reactions are not affected.

For example, when the enzyme in the enzymatic cycling reaction is a hydroxysteroid dehydrogenase (HSD), the substance serving as the substrate for the enzyme that selectively reduces NAD should preferably not have a steroid skeleton. Examples of substances that may serve as substrates without steroid skeletons include organic acids and amino acids, and examples of enzymes that selectively reduce NAD and have these substances as substrates include malate dehydrogenase, lactate dehydrogenase, hydroxybutyrate dehydrogenase, isocitrate dehydrogenase, glutamate dehydrogenase, leucine dehydrogenase, alanine dehydrogenase, phenylalanine dehydrogenase, serine dehydrogenase, valine dehydrogenase, glycine dehydrogenase, lysine dehydrogenase, tryptophan dehydrogenase and aspartate dehydrogenase.

For the enzyme that selectively reduces NAD and/or NADP, substrate specificity and the like are preferably also considered with respect to the labeling enzyme. For example, when an alkaline phosphatase is used as the labeling enzyme, an enzyme that uses a substance other than a substance having a phosphate group as a substrate is selected as the enzyme that selectively reduces NAD and/or NADP. Examples of enzymes having substrates that are substances that do not have phosphate groups include glutamate dehydrogenase, leucine dehydrogenase, alanine dehydrogenase, phenylalanine dehydrogenase, malate dehydrogenase, 3-hydroxybutyrate dehydrogenase, lactate dehydrogenase, glucose dehydrogenase, galactose dehydrogenase and the like.

Similarly, when a glucosidase, galactosidase, fructosidase or mannosidase is used as the labeling enzyme, an enzyme that uses a substance other than a substance containing a sugar residue such as glucose, galactose, fructose or mannose as a substrate is used as the enzyme that selectively reduces NAD and/or NADP. Examples of enzymes that use substances not containing sugar residues as substrates include glutamate dehydrogenase, leucine dehydrogenase, alanine dehydrogenase, phenylalanine dehydrogenase, malate dehydrogenase, 3-hydroxybutyrate dehydrogenase, lactate dehydrogenase and the like.

When a peroxidase is used as the labeling enzyme, on the other hand, an enzyme that uses a substance other than a substance having a peroxide structure as a substrate is used as the enzyme that selectively reduces NAD and/or NADP. Examples of enzymes that use substances not having peroxide structures as substrates include glutamate dehydrogenase, leucine dehydrogenase, alanine dehydrogenase, phenylalanine dehydrogenase, malate dehydrogenase, 3-hydroxybutyrate dehydrogenase, lactate dehydrogenase, glucose dehydrogenase, galactose dehydrogenase and the like.

Examples of the combination of enzyme and substrate used in the enzyme reaction system that selectively reduces NAD and/or NADP include, but are not limited to, the following.

(1) Glutamate dehydrogenase and glutamic acid
(2) Leucine dehydrogenase and leucine
(3) Alanine dehydrogenase and alanine
(4) Phenylalanine dehydrogenase and phenylalanine
(5) Serine dehydrogenase and serine
(6) Valine dehydrogenase and valine
(7) Lysine dehydrogenase and lysine
(8) Tryptophan dehydrogenase and tryptophan
(9) Aspartate dehydrogenase and aspartic acid
(10) Malate dehydrogenase and malic acid
(11) D-3-hydroxybutyrate dehydrogenase and D-3-hydroxybutyric acid
(12) Lactate dehydrogenase and lactic acid
(13) Glycerol dehydrogenase and glycerol
(14) Glycerophosphate dehyrogenase and glyceric acid
(15) Isocitrate dehydrogenase and isocitric acid In the method of the present invention, the concentrations of each component may be within the following ranges for example.

(1) Concentration range of antibody-enzyme complex or enzyme-labeled nucleic acid probe: 0.01 μg/ml to 1 mg/ml
(2) Concentration range of substrate for labeling enzyme: 1 μM to 500 mM
(3) Concentration range of NADH and/or NADPH: 0.01 mM to 50 mM
(4) Concentration range of thio-NAD and/or thio-NADP: 0.01 mM to 100 mM
(5) Concentration range of dehydrogenase (DH): 0.01 u/ml to 5000 u/ml
(6) Concentration range of enzyme of enzyme reaction system that selectively reduces NAD and/or NADP: 0.01 u/ml to 5000 u/ml
(7) Concentration range of substrate for enzyme of enzyme reaction system that selectively reduces NAD and/or NADP: 1 μM to 500 mM The reaction conditions are selected appropriately in consideration of the optimum temperature ranges of the labeling enzyme, the dehydrogenase (DH) and the enzyme of the enzyme reaction system that selectively reduces NAD and/or NADP. For example, a reaction temperature at room temperature is preferred because this simplifies the operations. However, the reaction may also be performed at a temperature higher than or lower than room temperature in consideration of the optimum temperature ranges of the labeling enzyme, the dehydrogenase (DH) and the enzyme of the enzyme reaction system that selectively reduces NAD and/or NADP.

The reaction time may be a time sufficient to accumulate enough thio-NADH and/or thio-NADPH to allow measurement of the generated amount of thio-NADH and/or thio-NADPH or measurement of a color change caused by the generated thio-NADH and/or thio-NADPH. However, the accumulated amount of thio-NADH and/or thio-NADPH necessary to allow measurement will differ according to the measurement conditions, and can be determined appropriately based on these conditions.

Cycling systems using thio-NAD(P) in the enzyme cycling system are unique cycling systems that have appeared relatively recently. In such a system, cycling is performed with both NAD(P)/NAD(P)H and its analog thio-NAD(P)/thio-NAD(P)H using a dehydrogenase (DH) that uses NAD(P)/NAD(P)H as a coenzyme, and the substrate of the dehydrogenase is amplified and assayed as thio-NAD(P)H (maximum absorption wavelength: 400 nm, molar extinction coefficient: 11,900). The measurement principles of thio-NAD(P) cycling are as stated above, but can also be explained as follows.

[C2]

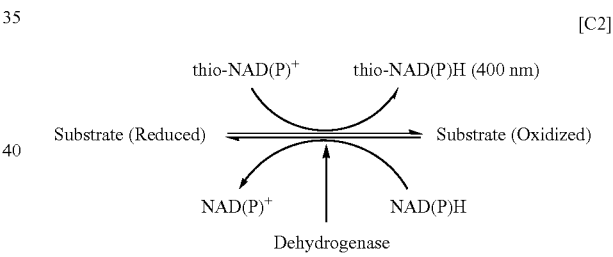

While the maximum absorption of NADH is 340 nm (molar extinction coefficient: 6,200), thio-NAD(P)H exhibits absorption in the visible range (maximum absorption wavelength: 400 nm, molar extinction coefficient: 11,900), and therefore has the advantage of being measurable with a common absorptiometer or colorimetric microplate reader.

In cycling systems using thio-NAD(P), some conventional techniques such as measurement of dehydrogenase activity based on increased absorption of NADH and quantification of its substrate have been improved in the method using thio-NAD by exploiting the advantage of measurement using a common absorptiometer or calorimetric microplate reader. PTL 1 represents the first case in which this cycling system is applied to raising the sensitivity of a detection system such as an enzyme immunoassay. In the present invention, it is now possible to further promote the amplification reaction and achieve greater sensitivity by combining a labeling enzyme with a cycling system and by further including an enzyme reaction system that selectively reduces NAD and/or NADP.

In the measurement method of the present invention, using the example of an enzyme immunoassay method, a product produced by an enzyme complex in combination with its associated substrate is used as the substrate in a subsequent enzymatic cycling reaction, and the absorption of thio-NAD(P)H produced by the enzymatic cycling reaction is then colorimetrically determined. Because enzyme cycling is performed with one kind of dehydrogenase in this reaction, the substrate in the enzymatic cycling reaction may be either a reduced substrate or an oxidized substrate. Moreover, because an enzyme reaction system that selectively reduces NAD and/or NADP is also included in the present invention, the NAD and/or NADP produced by the enzymatic cycling reaction is selectively reduced. Because the NAD and/or NADP is selectively reduced and NADH and/or NADPH is regenerated within the system, the progress of the enzymatic cycling reaction can be promoted and thio-NAD(P)H production can be increased without adding an excess of thio-NAD(P), NADH and/or NADPH at the beginning of the reaction.

(Enzyme Cycling Kit)

The present invention encompasses an enzyme cycling kit comprising an enzyme labeling a reactive carrier, its substrate, a cycling reaction enzyme and its coenzymes thio-NAD and NADH, and an enzyme reaction system (enzyme and substrate) that selectively reduces NAD and/or NADP.

A reactive carrier means an antibody, nucleic acid probe, lectin or the like having the activity of binding with an object of measurement. A substance suited to the object of measurement or a substance suited to the labeling enzyme and its substrate may be used as the reactive carrier, without any particular limitations.

More specifically, the present invention encompasses an enzyme cycling kit comprising a labeling enzyme and its substrate, a cycling reaction enzyme and its coenzymes thio-NAD and NADH, and an enzyme reaction system (enzyme and substrate) that selectively reduces NAD and/or NADP.

The kit of the present invention is an enzyme immunoassay kit comprising the reagents of (1) to (6) below:
(1) an enzyme labeling an antibody specific to a target protein antigen,
(2) a substrate for the enzyme of (1) above,
(3) a dehydrogenase,
(4) NADH and/or NADPH,
(5) thio-NAD and/or thio-NADP, and
(6) an enzyme reaction system that selectively reduces NAD and/or NADP.

The present invention is also a nucleic acid probe measurement kit comprising the reagents of (1) to (6) below:
(1) an enzyme labeling a nucleic acid probe that binds specifically to a target nucleic acid,
(2) a substrate for the enzyme of (1) above,
(3) a dehydrogenase,
(4) NADH and/or NADPH,
(5) thio-NAD and/or thio-NADP, and
(6) an enzyme reaction system that selectively reduces NAD and/or NADP.

The enzyme of the enzyme reaction system of (6) above is preferably a dehydrogenase.

In the enzyme reaction system of (6) above, preferably the substrate does not become a substrate for the enzyme of (1) and the dehydrogenase of (3), and the enzyme is preferably an enzyme that does not react with the substrate of (2) and with thio-NAD and/or thio-NADP of (5).

Preferably the dehydrogenase of (3) above is a hydroxysteroid dehydrogenase (HSD), and the enzyme of the enzyme reaction system of (6) above is a dehydrogenase other than a HSD (hydroxysteroid dehydrogenase).

Preferably the enzyme in the enzyme reaction system of (6) above is an enzyme selected from the enzyme group represented by EC number 1.1.1 having CH—OH as an electron donor, the enzyme group represented by EC number 1.2.1 having an aldehyde or oxo group as an electron donor, the enzyme group represented by EC number 1.3.1 having CH—CH as an electron donor, the enzyme group represented by EC number 1.4.1 having CH—NH$_2$ as an electron donor, and the enzyme group represented by EC number 1.5.1 having CH—NH as an electron donor.

For the labeling enzyme of (1), the dehydrogenase (DH) of (3), the enzyme of the enzyme reaction system of (6) and the substrates of these and the like, those explained under the methods of the present invention above may be used as is. For example, the enzyme of the antibody-labeling enzyme of (1) in the enzyme immunoassay kit and the enzyme of the nucleic acid probe-labeling enzyme of (1) in the nucleic acid probe measurement kit may each be at least one kind of enzyme selected from the group consisting of the alkaline phosphatases, glucosidases, galactosidases, fructosidases, mannosidases and peroxidases.

A commercial enzyme-labeled antibody or the like may also be used in combination with the constituent reagents of the kit of the present invention. This kit can be used in enzyme immunoassays using enzymatic cycling methods.

EXAMPLES

The present invention is explained in more detail below based on examples. However, these examples only exemplify the present invention, and are not intended to limit the present invention.

Example: Using Enzymatic Cycling Reaction to Measure *Mycobacterium Tuberculosis* Complex Using a monoclonal antibody to MPB64, a secretory protein specific to the *Mycobacterium tuberculosis* complex, an enzymatic cycling reaction was performed using alkaline phosphatase (ALP) as the labeling enzyme of the antibody, with 17β-methoxy-5β-androstane 3-phosphate (A3P) as the substrate of the labeling enzyme and 3α-hydroxysteroid dehydrogenase (3α-HSD) as the enzyme cycling enzyme, in combination with an enzyme reaction whereby NADH was produced by consuming the NAD produced by the previous reaction as a coenzyme.

Reference Example 1 (Sample Preparation)

*Mycobacterium bovis* BCG Tokyo strain (hereunder called "BCG") was seeded on Middlebrook 7H11 liquid medium, and cultured to a specific turbidity to obtain a culture supernatant. The resulting culture supernatant was adjusted to a McFarland No. 1 equivalent turbidity (equivalent to concentration 1×10$^8$ cfu/ml) to obtain a test sample.

Reference Example 2 (Preparation of Anti-MPB64 Monoclonal Antibody)

Purified MPB64 obtained by ordinary methods as in Reference Example 1 was used as an immunizing antigen to prepare monoclonal antibodies to the protein. The monoclonal antibodies were prepared by ordinary methods.

Ultimately, two clones were obtained of cells producing monoclonal antibodies reacting with MPB64. The antibodies produced by the respective clones were named monoclonal antibody BL001 and monoclonal antibody BL002.

Reference Example 3 (Preparation of ALP-Labeled Antibody)

The monoclonal antibody BL001 obtained in Reference Example 2 was dialyzed with 100 mM acetic acid buffer (pH 3.8). A 30-minute dialysis operation was performed 3 times. Pepsin was added to the antibody solution after dialysis to 5% based on the amount of the antibody, and the solution was heated for 2 hours at 37° C. and then neutralized by addition of 1.5 M tris-hydrochloric acid buffer (pH 8.8). Part of the reaction solution was subjected to SDS (sodium dodecyl sulfate)-polyacrylamide gel electrophoresis (SDS-PAGE), and after production of F(ab')$_2$ by pepsin digestion treatment had been confirmed, the solution was purified with a column packed with Superdex 200 pg (product of GE Healthcare Japan) to obtain a F(ab')$_2$ fraction. The concentration of the resulting F(ab')$_2$ solution was adjusted to 1 mg/ml.

0.1 ml of 0.1 M 2-mercaptoethylamine solution was added to 0.9 ml of the resulting F(ab')$_2$ solution, which was then subjected to reduction treatment by 90 minutes of heating at 37° C. Following the 90-minute reduction reaction, the reaction solution was purified with a column packed with Superdex 200 pg to obtain a Fab fraction.

0.1 ml of a 5 mM tris-hydrochloric acid buffer solution (pH 7.0, containing 5 mM MgCl$_2$, 0.1 mM ZnCl$_2$ and 50% glycerol) containing 17.14 mg/ml ALP was supplied to a PD-10 column (product of GE Healthcare Japan), and 50 mM sodium borate buffer solution (pH 7.6, containing 1 mM MgCl$_2$ and 0.1 mM ZnCl$_2$) was substituted for the buffer solution. The resulting ALP solution was adjusted to 1 mg/ml. 2.25 ml of a dimethylformamide solution (EMCS concentration 17 mg/ml) containing N-(6-maleimidocaproyloxy)succinimide (hereunder called "EMCS") was added to 0.5 ml of the ALP solution, which was then reacted for 30 minutes at 37° C. The reaction mixture was supplied to a PD-10 column, and 0.1 M tris-hydrochloric acid buffer solution (pH 7.0, containing 1 mM MgCl$_2$ and 0.1 mM ZnCl$_2$) was substituted to obtain a maleimidated ALP solution.

The Fab antibody solution prepared in the previous reaction was mixed with the maleimidated ALP solution, and reacted for a whole day and night at 4° C. The reaction solution was purified with a column packed with Superdex 200 pg to obtain an ALP-labeled Fab fraction. The resulting ALP-labeled Fab solution was concentrated to a predetermined concentration to prepare an ALP-labeled Fab antibody solution.

Reference Example 4 (Preparation of Monoclonal Antibody-Immobilized Microplate)

The monoclonal antibody BL002 obtained in Reference Example 2 was adjusted with 10 mM tris-hydrochloric acid buffered saline (pH 7.5, hereunder called "TBS") to 20 µg/ml. 100 µl of the resulting antibody solution was added to each well of a flat-bottomed microplate, and left standing for 1 hour at 37° C. This was then washed multiple times with TBS containing 0.05% Tween20, TBS solution containing 1% bovine serum albumin (hereunder called "BSA") was added 350 µl per well, and the microplate was blocked by being left standing for 1 hour at room temperature. The solution in the wells was removed, and the microplate was air dried to prepare a monoclonal antibody-immobilized microplate.

Comparative Example (MPB64 Measurement by Enzymatic Cycling Reaction: Conventional Method)

Measurement was performed using the ALP-labeled anti-MPB64 Fab antibody and an enzymatic cycling reaction reagent that was prepared as follows using A3P as the enzymatic cycling reaction substrate and 3α-HSD as the enzymatic cycling reaction enzyme.

Reaction Reagent 1
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase Measurement Methods The test sample prepared in Reference Example 1 was diluted 1×10$^5$ with a sample diluent (TBS containing 0.1% BSA and 0.01% Tween 20), and 100 µl of this was added to the monoclonal antibody-immobilized microplate prepared in Reference Example 4, and shaken for 1 hour at room temperature. The solution was then removed by suction from the wells, which were then washed 3 times with TBS containing 0.05% Tween 20, and 100 µl of an antibody solution containing the ALP-labeled Fab antibody prepared in Reference Example 3 at a concentration of 2.5 µg/ml was added and shaken for 1 hour at room temperature. The solution was removed by suction from the wells, which were then washed 3 times with TBS containing 0.05% Tween 20. 100 µl of the reaction reagent 1 was then added to each well, and heated to 37° C. as the absorbance of each well was measured at 5 minute intervals after addition of the reaction reagent using a 405 nm filter with a microplate reader (Corona SH-9000). The sample diluent alone without any added test sample was also measured in the same way to obtain a blank value, and absorbance (hereunder called "ΔO.D.") was calculated by subtracting the blank value from the measurement value. The resulting ΔO.D. values were plotted to obtain the graph shown in FIG. 1.

Example 1 (Measurement of MPB64 by Enzymatic Cycling Reaction in Combination With Glutamate Dehydrogenase)

Measurement was performed using the reaction reagent 2 shown below, which was prepared by adding (microbial) glutamate dehydrogenase and its enzyme substrate L-glutamate, as a reaction system for reducing the NAD generated by the enzymatic cycling reaction to NADH and recovering it, to the enzymatic cycling reaction reagent 1 using the ALP-labeled anti-MPB64 Fab antibody, A3P as the enzymatic cycling reaction substrate and 3α-HSD as the enzymatic cycling reaction enzyme.

Reaction Reagent 2
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml glutamate dehydrogenase
2.0 mM L-glutamate Measurement Methods The test sample prepared in Reference Example 1 was diluted $1\times10^5$ with a sample diluent (TBS containing 0.1% BSA and 0.01% Tween 20), and 100 µl of this was added to the monoclonal antibody immobilized microplate prepared in Reference Example 4, and shaken for 1 hour at room temperature. The solution was then removed by suction from the wells, which were then washed 3 times with TBS containing 0.05% Tween 20, and 100 µl of an antibody solution containing the ALP-labeled Fab antibody prepared in Reference Example 3 at a concentration of 2.5 µg/ml was added and shaken for 1 hour at room temperature. The solution was removed by suction from the wells, which were then washed 3 times with TBS containing 0.05% Tween 20. 100 µl of the reaction reagent 2 was then added to each well, and heated to 37° C. as the absorbance of each well was measured at 5 minute intervals after addition of the reaction reagent using a 405 nm filter with a microplate reader (Corona SH-9000) using a filter. The sample diluent alone without any added test sample was also measured in the same way to obtain a blank value, and absorbance (hereunder called "ΔO.D.") was calculated by subtracting the blank value from the measurement value.

Figure 2:
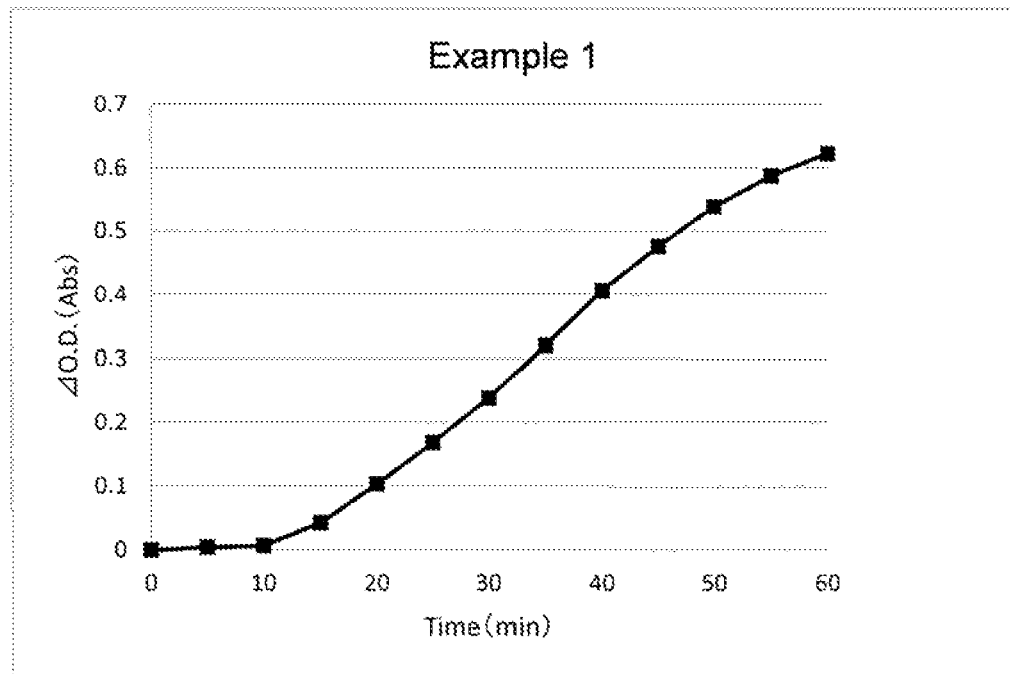
FIG. 2 shows measurement results obtained in Example 1 for MPB64 produced by an enzymatic cycling reaction incorporating glutamate dehydrogenase.

The resulting ΔO.D. values were plotted on the graph shown in FIG. 2. Since the ΔO.D. had not reached equilibrium even 60 minutes after addition of the reaction reagent 2, it was confirmed that a reaction occurred whereby the NAD generated by the enzymatic cycling reaction was consumed as a coenzyme to produce NADH in the course of an enzyme reaction converting L-glutamic acid to α-ketoglutaric acid by the action of glutamate dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 2 (Measurement of MPB64 by Enzymatic Cycling Reaction in Combination with Leucine Dehydrogenase)

Measurement was performed using the reaction reagent 3 shown below, which was prepared by adding leucine dehydrogenase (from *Bacillus* sp.) and its enzyme substrate L-leucine, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 3:
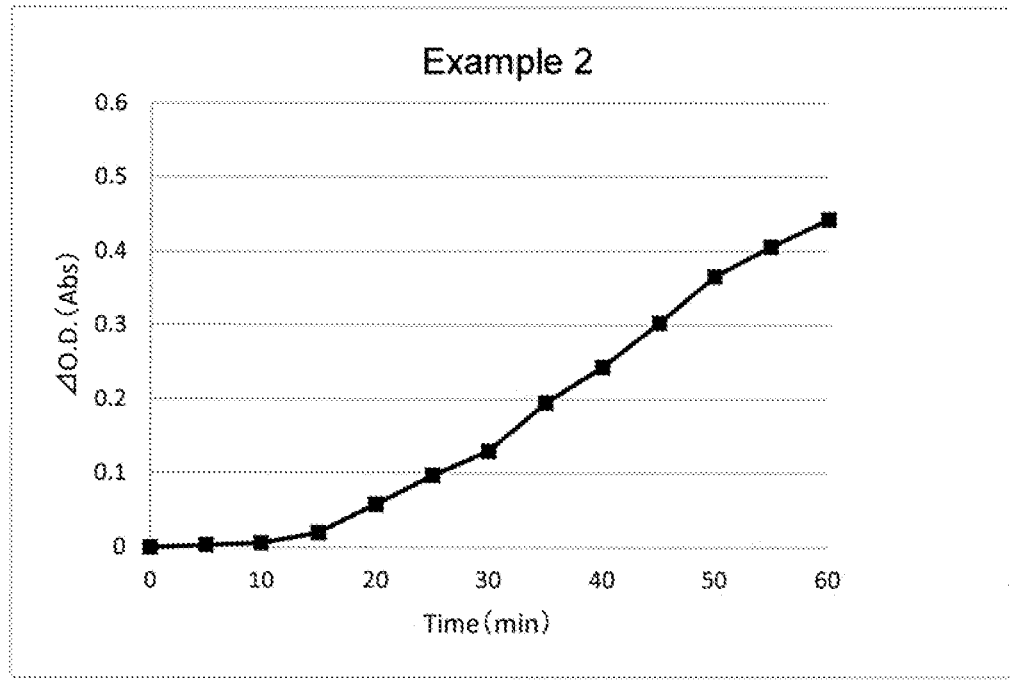
FIG. 3 shows measurement results obtained in Example 2 for MPB64 produced by an enzymatic cycling reaction incorporating leucine dehydrogenase.

Reaction Reagent 3
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml leucine dehydrogenase
2.0 mM L-leucine Measurement Methods Measurement was performed by the methods described in Example 1. The resulting ΔO.D. values were plotted to obtain the graph shown in FIG. 3.

Since the ΔO.D. had not reached equilibrium even 60 minutes after addition of the reaction reagent 3, it was confirmed that a reaction occurred whereby the NAD generated by the enzymatic cycling reaction was consumed as a coenzyme to produce NADH in the course of an enzyme reaction converting L-leucine to 4-methyl-2-oxopentanoic acid by the action of leucine dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 3 (Measurement of MPB64 by Enzymatic Cycling Reaction in Combination with Alanine Dehydrogenase)

Measurement was performed using the reaction reagent 4 shown below, which was prepared by adding alanine dehydrogenase (from *E. coli* genetically modified by *Bacillus cereus*) and its enzyme substrate L-alanine, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 4:
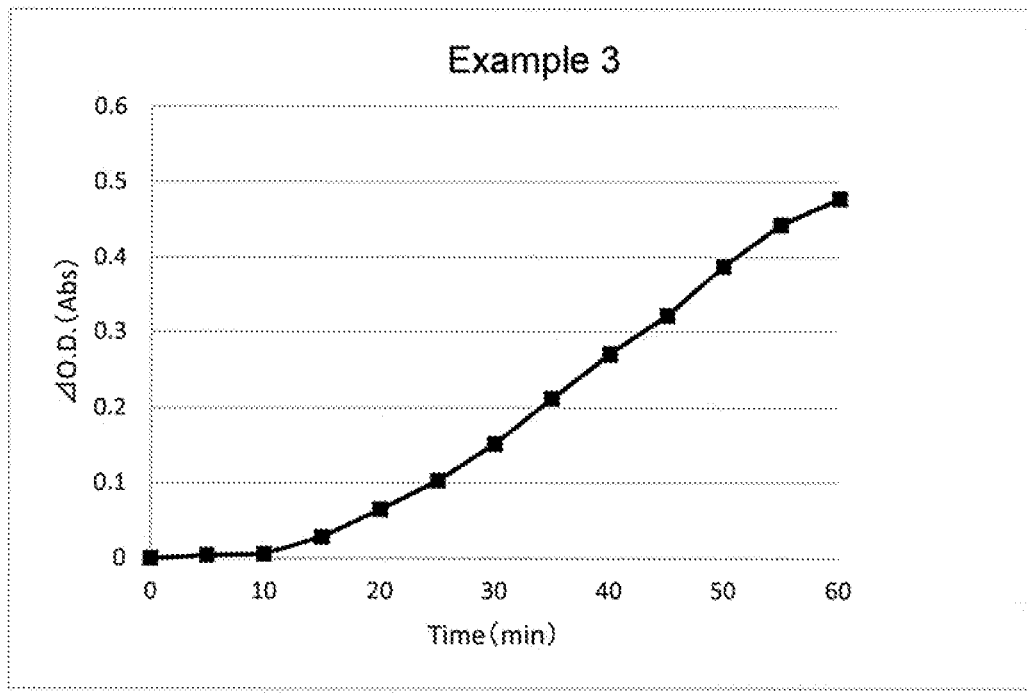
FIG. 4 shows measurement results obtained in Example 3 for MPB64 produced by an enzymatic cycling reaction incorporating alanine dehydrogenase.

Reaction Reagent 4
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml alanine dehydrogenase
2.0 mM L-alanine Measurement Methods Measurement was performed by the methods described in Example 1. The resulting ΔO.D. values were plotted to obtain the graph shown in FIG. 4.

Since the ΔO.D. had not reached equilibrium even 60 minutes after addition of the reaction reagent 4, it was confirmed that a reaction occurred whereby the NAD generated by the enzymatic cycling reaction was consumed as a coenzyme to produce NADH in the course of an enzyme reaction converting L-alanine to pyruvic acid by the action of alanine dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 4 (Measurement of MPB64 by Enzymatic Cycling Reaction in Combination with Phenylalanine Dehydrogenase)

Measurement was performed using the reaction reagent 5 shown below, which was prepared by adding L-phenylalanine dehydrogenase (from *Sporosarcina* sp.) and its enzyme substrate L-phenylalanine, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 5:
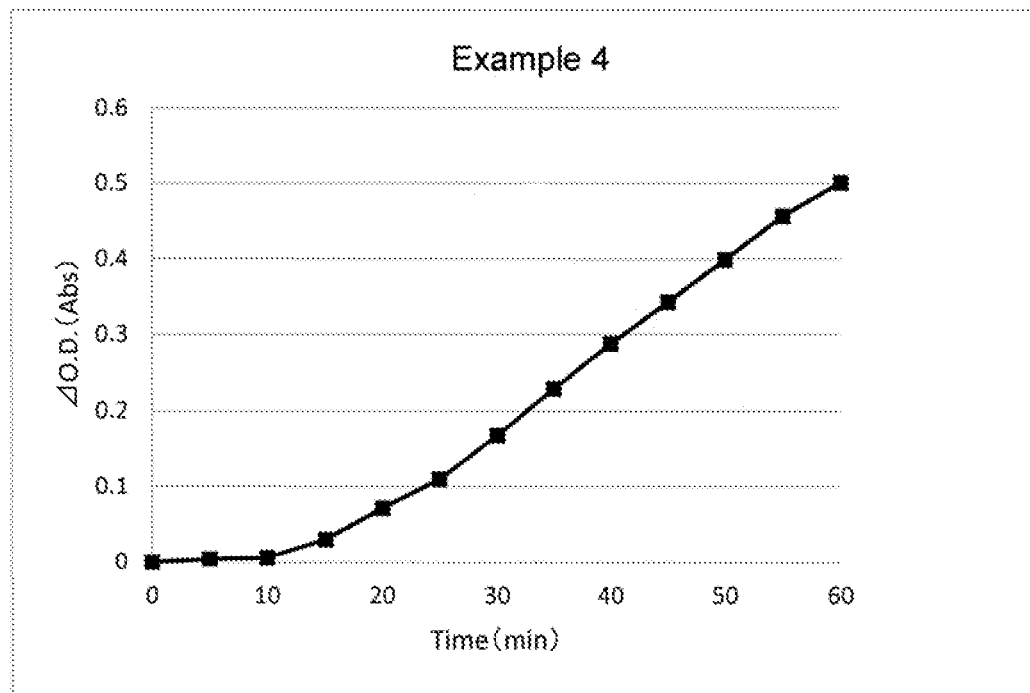
FIG. 5 shows measurement results obtained in Example 4 for MPB64 produced by an enzymatic cycling reaction incorporating phenylalanine dehydrogenase.

Reaction Reagent 5
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml phenylalanine dehydrogenase
2.0 mM L-phenylalanine
Measurement Methods Measurement was performed by the methods described in Example 1. The resulting ΔO.D. values were plotted to obtain the graph shown in FIG. 5.

Since the ΔO.D. had not reached equilibrium even 60 minutes after addition of the reaction reagent 5, it was confirmed that a reaction occurred whereby the NAD generated by the enzymatic cycling reaction was consumed as a coenzyme to produce NADH in the course of an enzyme reaction converting L-phenylalanine to phenylpyruvic acid by the action of L-phenylalanine dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 5 (Measurement of MPB64 by Enzymatic Cycling Reaction in Combination with Malate Dehydrogenase)

Measurement was performed using the reaction reagent 6 shown below, which was prepared by adding (microbial) malate dehydrogenase and its enzyme substrate L-malate, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 6:
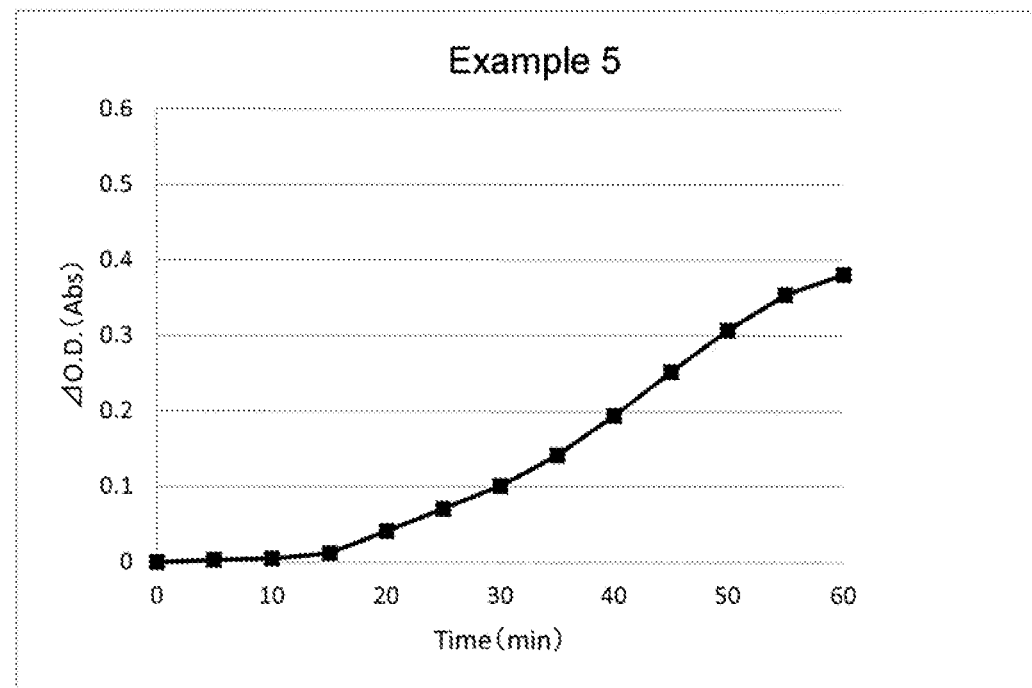
FIG. 6 shows measurement results obtained in Example 5 for MPB64 produced by an enzymatic cycling reaction incorporating malate dehydrogenase.

Reaction Reagent 6
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml malate dehydrogenase
2.0 mM L-malate
Measurement Methods Measurement was performed by the methods described in Example 1. The resulting ΔO.D. values were plotted to obtain the graph shown in FIG. 6.

Since the ΔO.D. had not reached equilibrium even 60 minutes after addition of the reaction reagent 6, it was confirmed that a reaction occurred whereby the NAD produced by the enzymatic cycling reaction was consumed as a coenzyme to produce NADH in the course of an enzyme reaction converting malic acid to oxaloacetic acid by the action of malate dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 6 (Measurement of MPB64 by Enzymatic Cycling Reaction in Combination with D-3-Hydroxybutyrate Dehydrogenase)

Measurement was performed using the reaction reagent 7 shown below, which was prepared by adding D-3-hydroxybutyrate dehydrogenase (from *Pseudomonas* sp.) and its enzyme substrate D-3-hydroxybutyrate, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 7:
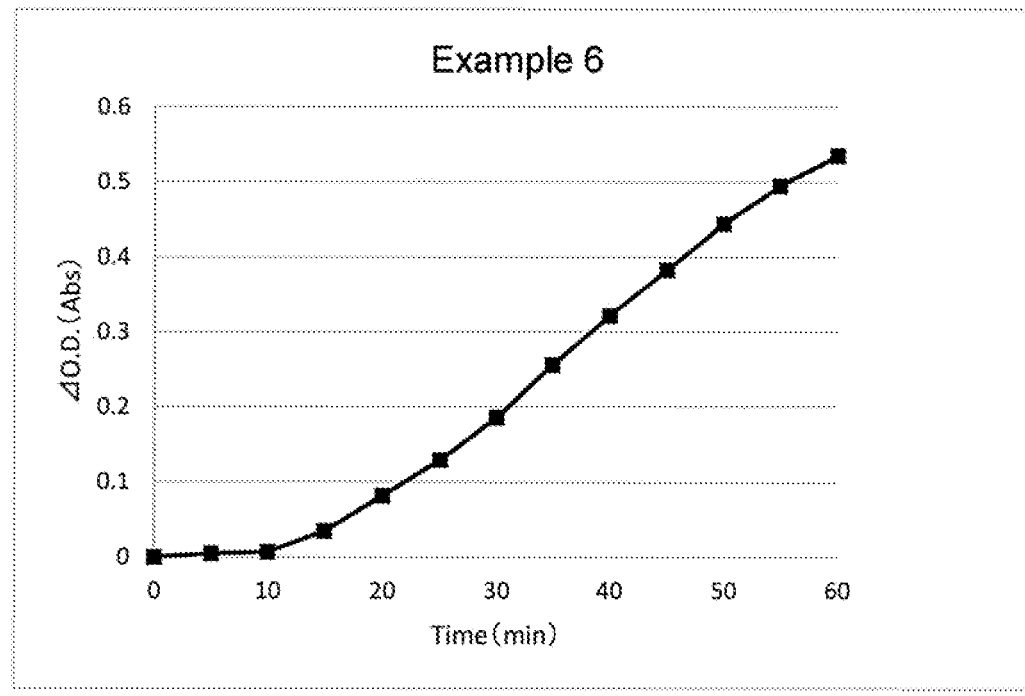
FIG. 7 shows measurement results obtained in Example 6 for MPB64 produced by an enzymatic cycling reaction incorporating D-3-hydrobutyrate dehydrogenase.

Reaction Reagent 7
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml hydroxybutyrate dehydrogenase
2.0 mM D-3-hydroxybutyrate
Measurement Methods Measurement was performed by the methods described in Example 1. The resulting ΔO.D. values were plotted to obtain the graph shown in FIG. 7.

Since the ΔO.D. had not reached equilibrium even 60 minutes after addition of the reaction reagent 7, it was confirmed that a reaction occurred in which the NAD produced by the enzymatic cycling reaction was consumed as a coenzyme to produce NADH in the course of an enzyme reaction converting D-3-hydroxybutyrate to acetoacetic acid by the action of D-3-hydroxybutyrate dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 7 (Measurement of MPB64 by Enzymatic Cycling Reaction in Combination with Lactate Dehydrogenase)

Measurement was performed using the reaction reagent 8 shown below, which was prepared by adding L-lactate dehydrogenase (from recombinant *E. coli*) and its enzyme substrate L-lactate, as a reaction system for reducing the NAD generated by the enzymatic cycling reaction to NADH and recovering it, to the enzymatic cycling reaction reagent 1 using the ALP-labeled anti-MPB64 Fab antibody, A3P as an enzymatic cycling reaction substrate and 3α-HSD as an enzymatic cycling reaction enzyme.

Figure 8:
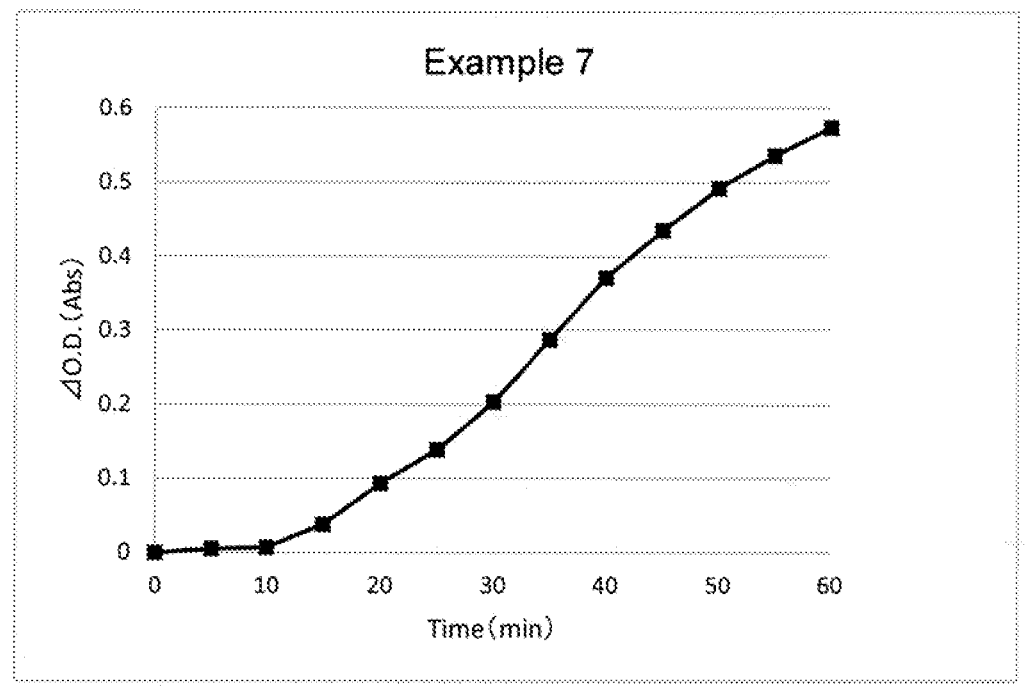
FIG. 8 shows measurement results obtained in Example 7 for MPB64 produced by an enzymatic cycling reaction incorporating lactate dehydrogenase.

Reaction Reagent 8
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml lactate dehydrogenase
2.0 mM L-lactate Measurement Methods Measurement was performed by the methods described in Example 1. The resulting ΔO.D. values were plotted to obtain the graph shown in FIG. 8.

Since the ΔO.D. had not reached equilibrium even 60 minutes after addition of the reaction reagent 8, it was confirmed that a reaction occurred in which the NAD produced by the enzymatic cycling reaction was consumed as a coenzyme to produce NADH in the course of an enzyme reaction converting L-lactate to pyruvic acid by the action of L-lactate dehydrogenase, and that reduction of NADH concentration in the enzymatic cycling reaction reagent was suppressed and a reaction producing thio-NADH progressed continuously as a result. Consequently, this was confirmed to be a highly sensitive measurement method with a broad measurement range in comparison with the conventional measurement method using enzyme cycling shown in Comparative Example 1.

Example 8

Using the reaction reagent 2 prepared in Example 1, MPB64 in test samples obtained by diluting the test sample prepared in Reference Example 1 with sample diluent at dilution rates of $1\times10^7$, $1\times10^6$, $1\times10^5$, $1\times10^4$ and $1\times10^3$ was measured by an enzymatic cycling method incorporating a reaction that produced NADH by consuming NAD as a coenzyme (hereunder, "improved method"). As a control, test samples with the same dilution sequence were measured by a conventional enzymatic cycling method (conventional method, similar to the method described in PTL 2) using the reaction reagent 1 prepared in Comparative Example 1.

Figure 9:
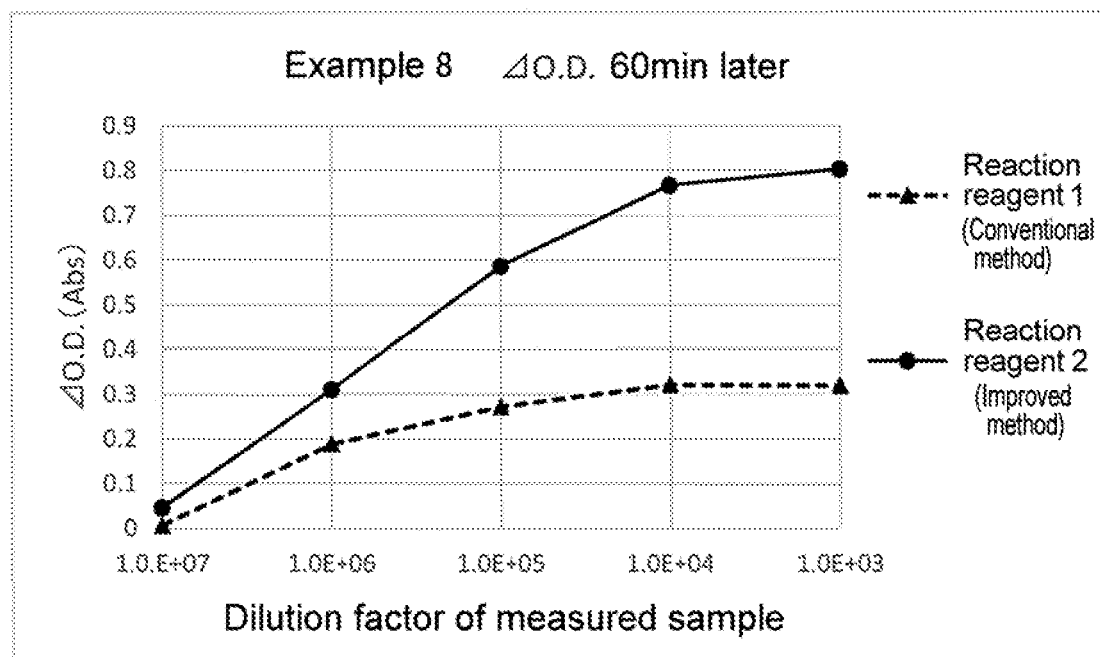
FIG. 9 shows measurement results obtained in Example 8 for MPB64 produced by an enzymatic cycling reaction incorporating glutamate dehydrogenase.

Reaction Reagent 1 (Conventional Method)
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
Reaction Reagent 2 (Improved Method)
0.1 M tris-hydrochloric acid buffer (pH 9.0)
2.0 mM thio-NAD
0.5 mM NADH
0.1 mM 17β-methoxy-5β-androstane 3-phosphate
20 U/ml 3α-hydroxysteroid dehydrogenase
20 U/ml glutamate dehydrogenase
2.0 mM L-glutamate
Measurement Methods Measurement was performed by two methods using the reaction reagent 1 (conventional method) and reaction reagent 2 (improved method) with test samples prepared at dilution rates of $1\times10^7$, $1\times10^6$, $1\times10^5$, $1\times10^4$ and $1\times10^3$. The measurement was otherwise performed according to the methods described in Example 1. The ΔO.D. values 60 minutes after addition of the reaction reagents were plotted on the graph shown in FIG. 9.

In comparison with the conventional method using the reaction reagent 1, it was confirmed that in the improved method using the reaction reagent 2, absorbance maintained linearity for each test sample at each dilution rate within a broad range, and the dilution rate at which the test samples reached peak absorbance was low, meaning that quantitative measurement was possible even with highly concentrated test samples. This is thought to be because an enzyme reaction that converts L-glutamate to α-ketoglutaric acid by the action of glutamate dehydrogenase proceeds simultaneously in the enzymatic cycling reaction system, and the NAD generated in the reaction system as a result of the enzymatic cycling reaction is consumed as a coenzyme by the glutamate dehydrogenase to produce NADH, thereby suppressing a reduction in NADH concentration in the reaction system (maintaining NADH concentration in comparison with conventional methods) and progressing a reaction producing thio-NADH. Consequently, the method of the present invention is confirmed to be a measurement method having greater sensitivity and a broader measurement range than conventional methods.

INDUSTRIAL APPLICABILITY

The present invention can be applied favorably to a wide range of fields, including clinical testing and food testing, that require highly sensitive and simple measurement.

The invention claimed is:

1. An enzymatic measurement method using an antibody-enzyme complex, the method being implemented in which an enzyme reaction product of the antibody-enzyme complex is assayed by generating thio-NADH and/or thio-NADPH by an enzymatic cycling reaction using NADH and/or NADPH, thio-NAD and/or thio-NADP and a dehydrogenase (DH), followed by:
   i) measuring the generated thio-NADH and/or thio-NADPH, or
   ii) measuring a color change caused by the generated thio-NADH and/or thio-NADPH, wherein
   an enzyme reaction system that selectively reduces the NAD and/or NADP generated from NADH and/or NADPH by the enzymatic cycling reaction is included in the enzymatic cycling reaction system,
   wherein the enzyme reaction system that selectively reduces the NAD and/or NADP uses a substrate that does not become a substrate for the enzyme of the antibody-enzyme complex and a substrate for the enzyme of the enzymatic cycling reaction, and an enzyme that does not react with the substrate for the enzyme of the antibody-enzyme complex and the substrate of the enzyme of the enzymatic cycling reaction; and
   wherein the combination of enzyme and substrate used in the enzyme reaction system that selectively reduces NAD and/or NADP is selected from the group consisting of:
   (i) glutamate dehydrogenase and glutamic acid;
   (ii) leucine dehydrogenase and leucine;
   (iii) alanine dehydrogenase and alanine;
   (iv) phenylalanine dehydrogenase and phenylalanine;
   (v) serine dehydrogenase and serine;
   (vi) valine dehydrogenase and valine;
   (vii) tryptophan dehydrogenase and tryptophan; and
   (viii) aspartate dehydrogenase and aspartic acid.

2. The method according to claim 1, wherein the enzyme in the enzymatic cycling reaction is a hydroxysteroid dehydrogenase.

3. The method according to claim 1, wherein the enzyme of the antibody-enzyme complex is at least one of enzyme selected from the group consisting of alkaline phosphatases, glucosidases, galactosidases, fructosidases, mannosidases and peroxidases.

* * * * *